United States Patent
Chen et al.

(10) Patent No.: US 8,449,497 B2
(45) Date of Patent: *May 28, 2013

(54) CATHETER HAVING AN IMPROVED BALLOON-TO-CATHETER BOND

(75) Inventors: John Chen, Plymouth, MN (US); Nie Tang, Maple Grove, MN (US); Ed Parsonage, Saint Paul, MN (US); Paul Miller, Vadnais Heights, MN (US); Lixiao Wang, Long Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,334

(22) Filed: Mar. 28, 2011

(65) Prior Publication Data
US 2011/0172599 A1 Jul. 14, 2011

Related U.S. Application Data

(63) Continuation of application No. 10/764,405, filed on Jan. 23, 2004, now Pat. No. 7,914,486, which is a continuation-in-part of application No. 10/027,417, filed on Dec. 20, 2001, now Pat. No. 6,923,787.

(51) Int. Cl.
*A61M 29/00* (2006.01)

(52) U.S. Cl.
USPC .................. 604/103; 604/96.01; 604/915

(58) Field of Classification Search
USPC ............ 604/523, 96.01, 103, 103.05, 103.06, 604/915; 606/191, 192, 194, 108; 428/35.2, 428/35.7
See application file for complete search history.

(56) References Cited

U.S. PATENT DOCUMENTS

| 4,960,410 A | 10/1990 | Pinchuk |
| 5,047,045 A | 9/1991 | Arney et al. |
| 5,100,381 A | 3/1992 | Burns |
| 5,108,415 A | 4/1992 | Pinchuk et al. |
| 5,156,594 A | 10/1992 | Keith |
| 5,195,969 A | 3/1993 | Wang et al. |
| 5,254,090 A | 10/1993 | Lombardi et al. |
| 5,270,086 A | 12/1993 | Hamlin |
| 5,314,386 A | 5/1994 | Eide et al. |
| 5,342,386 A | 8/1994 | Trotta |

(Continued)

FOREIGN PATENT DOCUMENTS

| EP | 0 553 960 | 8/1993 |
| EP | 0 846 472 | 6/1998 |

(Continued)

OTHER PUBLICATIONS

Information Sheet: "Riding the Wave with Hytrel Thermoplastic Polyester Elastomer," Innovare, Apr. 2001, p. 41.

*Primary Examiner* — Kevin C Sirmons
*Assistant Examiner* — Deanna K Hall
(74) *Attorney, Agent, or Firm* — Seagre, Tufte & Wickhem, LLC

(57) ABSTRACT

A balloon catheter assembly includes a first tubular member with a proximal portion and a distal portion and a lumen extending between the proximal portion and the distal portion. A balloon has a proximal waist length, a distal waist length and an expandable region therebetween disposed about the distal portion. A tie layer is disposed between the proximal waist length or distal waist length and the first tubular member. The tie layer comprises a polyester polymer and a polyamide polymer.

9 Claims, 3 Drawing Sheets

U.S. PATENT DOCUMENTS

| | | |
|---|---|---|
| 5,344,401 A | 9/1994 | Radisch et al. |
| 5,358,486 A | 10/1994 | Saab |
| 5,425,712 A | 6/1995 | Goodin |
| 5,439,454 A | 8/1995 | Lo et al. |
| 5,478,320 A | 12/1995 | Trotta |
| 5,478,620 A | 12/1995 | Mugge et al. |
| 5,499,973 A * | 3/1996 | Saab .................. 604/96.01 |
| 5,501,759 A | 3/1996 | Forman |
| 5,512,051 A | 4/1996 | Wang et al. |
| 5,533,985 A | 7/1996 | Wang |
| 5,538,510 A | 7/1996 | Fontirroche et al. |
| 5,545,151 A | 8/1996 | O'Connor et al. |
| 5,549,552 A | 8/1996 | Peters et al. |
| 5,587,125 A | 12/1996 | Roychowdhury |
| 5,603,991 A | 2/1997 | Kupiecki et al. |
| 5,755,690 A | 5/1998 | Saab |
| 5,769,819 A | 6/1998 | Schwab et al. |
| 5,789,018 A | 8/1998 | Engelson et al. |
| 5,797,877 A | 8/1998 | Hamilton et al. |
| 5,820,594 A | 10/1998 | Fontirroche et al. |
| 5,824,173 A | 10/1998 | Fontirroche et al. |
| 5,843,032 A | 12/1998 | Kastenhofer |
| 5,876,376 A | 3/1999 | Schwab et al. |
| 5,902,631 A | 5/1999 | Wang et al. |
| 6,004,289 A | 12/1999 | Saab |
| 6,010,521 A | 1/2000 | Lee et al. |
| 6,020,071 A | 2/2000 | Watson |
| 6,027,477 A | 2/2000 | Kastenhofer |
| 6,086,556 A | 7/2000 | Hamilton et al. |
| 6,106,889 A | 8/2000 | Beavers et al. |
| 6,132,824 A | 10/2000 | Hamlin |
| 6,136,258 A | 10/2000 | Wang et al. |
| 6,165,166 A | 12/2000 | Samuelson et al. |
| 6,179,811 B1 | 1/2001 | Fugoso et al. |
| 6,217,547 B1 * | 4/2001 | Lee .................. 604/96.01 |
| 6,319,228 B1 | 11/2001 | Kastenhofer |
| 6,325,814 B1 | 12/2001 | Euteneuer et al. |
| 6,464,683 B1 | 10/2002 | Samuelson et al. |
| 6,471,673 B1 | 10/2002 | Kastenhofer |
| 6,482,348 B1 | 11/2002 | Wang et al. |
| 6,488,655 B1 | 12/2002 | Wantink et al. |
| 6,530,938 B1 | 3/2003 | Lee et al. |
| 6,659,977 B2 | 12/2003 | Kastenhofer |
| 7,914,486 B2 * | 3/2011 | Chen et al. .................. 604/103 |
| 2002/0022824 A1 | 2/2002 | Kastenhofer |
| 2002/0165523 A1 | 11/2002 | Chin et al. |
| 2003/0088265 A1 | 5/2003 | Kastenhofer |
| 2003/0120207 A1 | 6/2003 | Wang |
| 2003/0138582 A1 | 7/2003 | Miller et al. |

FOREIGN PATENT DOCUMENTS

| | | |
|---|---|---|
| EP | 0 873 759 | 10/1998 |
| WO | 03/053508 | 7/2003 |
| WO | 03/066121 | 8/2003 |

* cited by examiner

CATHETER HAVING AN IMPROVED BALLOON-TO-CATHETER BOND

CROSS REFERENCE TO RELATED APPLICATIONS

This application is a continuation of co-pending U.S. application Ser. No. 10/764,405, filed Jan. 23, 2004, which is a continuation-in-part of U.S. application Ser. No. 10/027,417, filed Dec. 20, 2001, now U.S. Pat. No. 6,923,787 and entitled CATHETER HAVING AN IMPROVED BALLOON-TO-CATHETER BOND, the entire disclosures of which are both hereby incorporated herein by reference.

TECHNICAL FIELD

The present invention relates generally to the field of medical devices having an expandable balloon disposed proximate the distal portion of a shaft. More specifically, the present invention relates to improved physical properties, processing and performance of a bond formed between the waist of an expandable balloon and the portion of the tubular member of a catheter shaft to which it is bonded.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guidewire, possibly in combination with other intravascular devices such as stents. A typical balloon catheter has an elongate shaft with a balloon attached proximate the distal end and a manifold attached to the proximal end. In use, the balloon catheter is advanced over the guidewire such that the balloon is positioned adjacent a restriction in a diseased vessel. The balloon is then inflated, and the restriction in the vessel is opened.

There are three basic types of intravascular catheters for use in such procedures including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

Manufacturers are constantly in search of materials and designs that enhance the performance of their intravascular catheters. One particular source of improvement has been the incorporation of performance-enhancing polymeric materials into their intravascular catheter designs. Certain polymeric materials enable the catheter to be more lubricious, thereby aiding the advancement of a guidewire within the body of the catheter. Other polymeric materials make particular sections of the catheter more rigid, thereby aiding the catheter in its advancement through the patient's anatomy. The primary drawback to using specialized polymeric materials is that often the individual polymers forming the structural components are incompatible with one another. This is a particular problem for manufacturers who must combine the individual components to form a single operable intravascular catheter.

One solution to the use of incompatible polymers has been to place a layer between the two incompatible polymeric structural components that is sufficiently bondable to either component. In effect, this distinct layer "ties" the two structural components together, thereby receiving its commonly referred to name as a tie layer. Tie layers have been extruded over the length of intravascular catheters. This added layer, regardless of its thickness, affects the performance characteristics of an intravascular catheter shaft incorporating the tie layer.

Several performance characteristics that are important to intravascular catheters include pushability, trackability and crossability. Pushability refers to the catheter's ability to transmit force from the proximal end of the catheter to the distal end of the catheter. Trackability refers to the catheter's ability to navigate tortuous vasculature. Crossability refers to the catheter's ability to navigate the balloon catheter across narrow restrictions in the vasculature, such as stenosed vessels or fully and partially deployed stents. All of the above performance characteristics are interrelated and depend on the design of the catheter shaft over its length.

It is a manufacturing goal to reduce the profile of a manufactured intravascular catheter. A reduced profile catheter is less likely to positively engage the surrounding vascular walls. Additionally, a reduced profile catheter is also more likely to cross and re-cross over a stenosed region or a deployed stent.

SUMMARY OF SOME EMBODIMENTS

The invention provides several alternative designs, materials and methods of manufacturing alternative medical device structures and assemblies.

Accordingly, an example embodiment of the invention can be found in a balloon catheter assembly that includes a first tubular member with a proximal portion and a distal portion and a lumen extending between the proximal portion and the distal portion. A balloon has a proximal waist length, a distal waist length and an expandable region therebetween disposed about the distal portion. A tie layer is disposed between the proximal waist length or distal waist length and the first tubular member. The tie layer comprises a polyester polymer and a polyamide polymer.

Another example embodiment of the invention can be found in a balloon catheter assembly that includes a first polyamide tubular member having a proximal portion and a distal portion with a lumen extending between the proximal portion and the distal portion. A polyethylene terephthalate balloon has a proximal waist length, a distal waist length and an expandable region therebetween disposed about the distal portion. A tie layer is disposed between the proximal waist length or distal waist length and the first tubular member, wherein the tie layer comprises a polyester polymer and a polyamide polymer.

Another example embodiment of the invention can be found in a method for improved bonding between an expandable balloon and a catheter shaft, the method including the steps of: providing a first polyamide tubular member having a proximal portion and a distal portion with a lumen extending between the proximal portion and the distal portion; disposing a tie layer on the distal portion of the first polyamide tubular member, wherein the tie layer comprises a polyester polymer and a polyamide polymer; and disposing a polyethylene terephthalate balloon having a proximal waist length, a distal waist length and an expandable region therebetween disposed on the tie layer.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
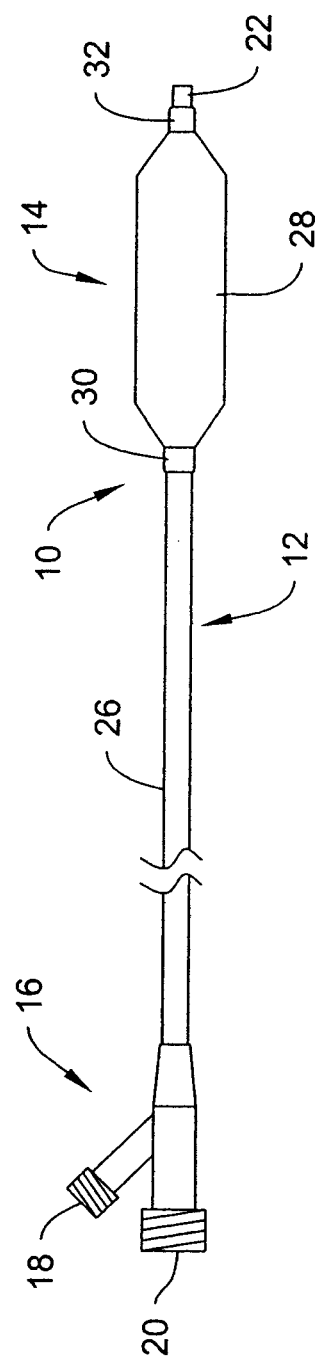
FIG. 1 is a plan view of a balloon catheter in accordance with the present invention having a distal balloon region.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

For example, although discussed with specific reference to balloon catheters in the particular embodiments described herein, the invention may be applicable to a variety of medical devices that are adapted to be advanced into the anatomy of a patient through an opening or lumen. For example, the invention may be applicable to fixed wire devices, other catheters (e.g., balloon, stent delivery, etc.), drive shafts for rotational devices such as atherectomy catheters and IVUS catheters, endoscopic devices, laproscopic devices, embolic protection devices, spinal or cranial devices, and other such devices.

FIG. 1 is a plan view of a balloon catheter 10 that is representative of one type of catheter that can incorporate the present invention. Other intravascular catheter embodiments are additionally suitable without deviating from the spirit and scope of the present invention. For example, intravascular catheters suitable for incorporating the present invention also include over-the-wire (OTW) catheters, fixed-wire (FW) catheters, single-operator-exchange (SOE) catheters and the like.

The balloon catheter 10 includes a shaft assembly 12 and a balloon assembly 14 connected proximate the distal end of the shaft assembly 12. A conventional manifold assembly 16 is connected to the proximal end of the shaft assembly 12. The proximal end of the shaft assembly 12 extends into the manifold assembly 16 and is bonded to the shaft assembly 12. Manifold ports 18 and 20 extend from the manifold assembly 16 for attaching and fluidly connecting ancillary apparatus to a lumen extending through the balloon catheter 10. Each manifold port includes a lumen terminating into either a common lumen or a dedicated lumen extending within the shaft assembly 12 (e.g., a guidewire lumen). Functionally, the manifold assembly 16 additionally provides a convenient place for a physician to apply longitudinal or rotational forces in order to manipulate the catheter 10 during a medical procedure.

Referring specifically to FIG. 1, the manifold assembly 16 illustrated includes two luer-type manifold ports 18 and 20. In alternative embodiments, the union between the manifold assembly 16 and ancillary medical devices (not shown) is completed using alternative connectors.

The shaft assembly 12 may comprises an outer tubular member 26 which is co-axially disposed about an inner tubular member 22 to define an annular inflation lumen therebetween over a substantial portion of the length of the catheter 10. The outer tubular member 26 may have an outer diameter ranging from 0.030 inches to 0.050 inches with a wall thickness ranging from 0.0028 inches to 0.0044 inches. Materials used to form the outer tubular member 26 may vary to achieve the stiffness desired for the shaft assembly 12. Nylon and polyamides are examples of suitable polymers for outer tubular members. Rigidity may additionally be imparted to the outer tubular member 26 by incorporating a braid on or within the outer tubular member 26.

A polyamide may be also used to form the shaft assembly 12, the outer tubular member 26 or inner tubular member 22. Polyamides, as well as polyether block amides, can be utilized. Polyether block amide (PEBA) is commercially available as PEBAX® from Atochem Inc, Glen Rock, N.J.

The inner tubular member 22 defines a guidewire lumen, which provides a passage for a guidewire (not shown). The inner tubular member 22 can be made of the same material as the outer tubular member 26. In alternative embodiments, the inner tubular member 22 can be lined with a generally lubricious material such as high density polyethylene (HDPE) or polytetrafluoroethylene (PTFE). The proximal end of the inner tubular member 22 may have an outside diameter ranging from 0.022 inches to 0.045 inches. The inner diameter of the inner tubular member 22 may be approximately 0.018 inches to 0.038 inches, allowing for use of a 0.014-inch guidewire. The inner tubular member 22 can have a wall thickness ranging from 0.0026 inches to 0.004 inches, or about 0.0032 inches. The outside diameter-to-wall thickness ratio can be sufficiently small to minimize the propensity for the shaft assembly 12, and more specifically, the inner tubular member 22 to kink.

Figure 2:
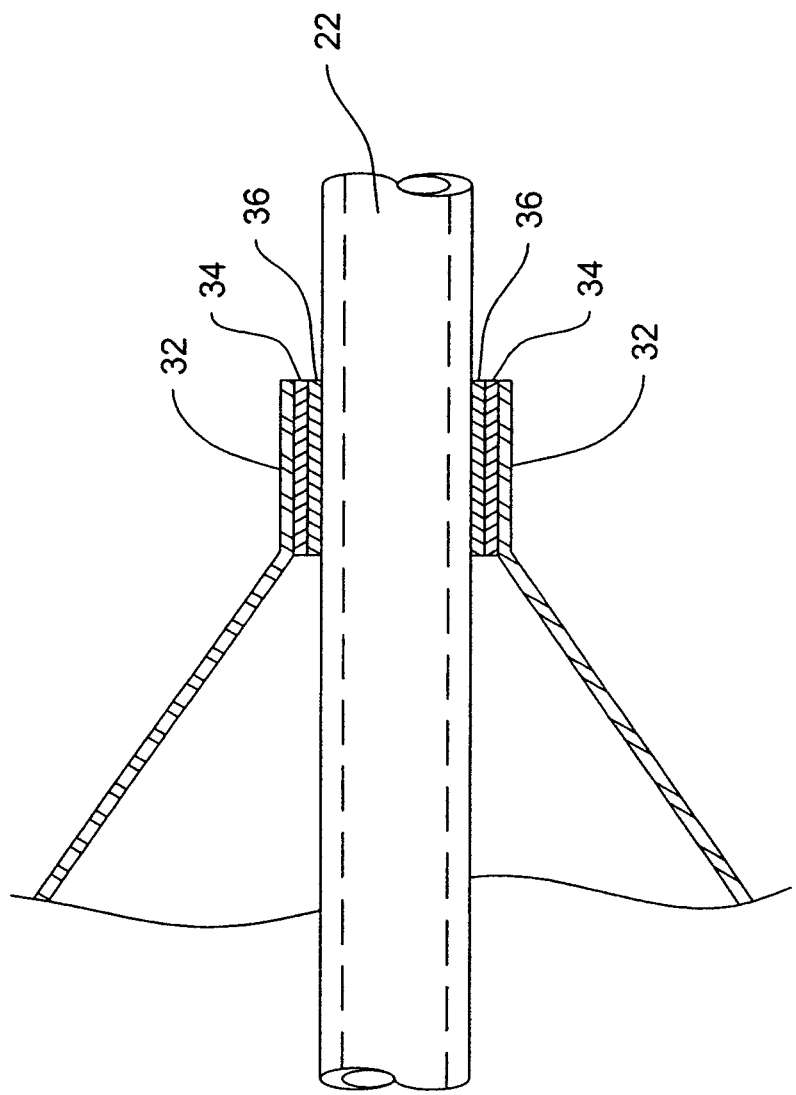
FIG. 2 is an enlarged partial cross-sectional view of the area surrounding the distal balloon waist of the balloon catheter of FIG. 1.
Figure 3:
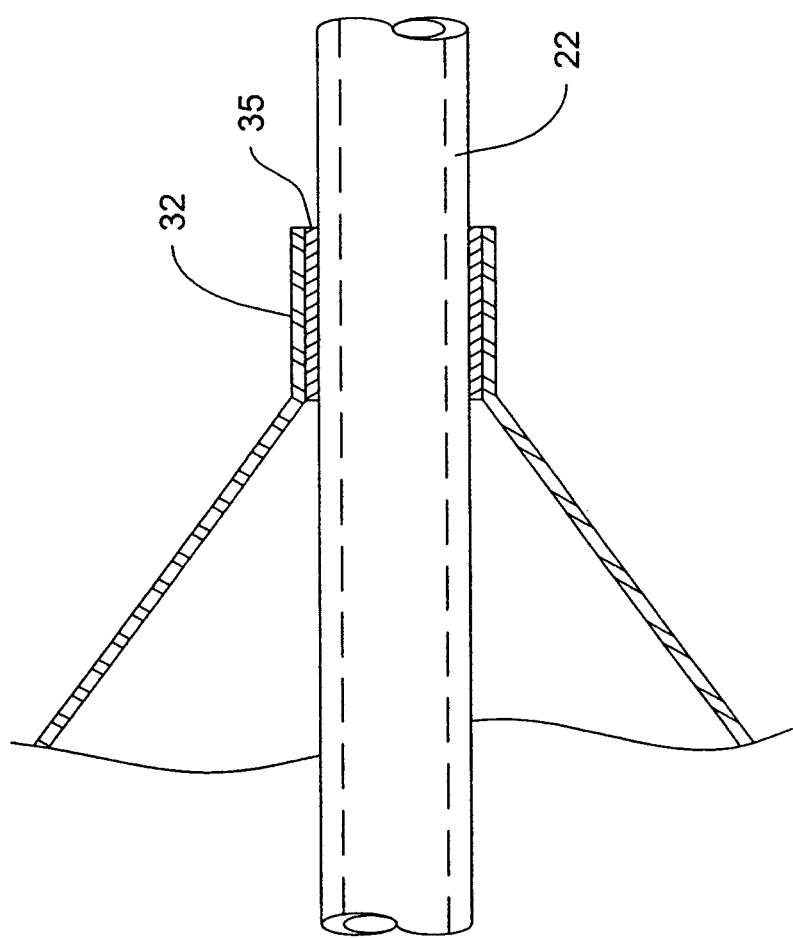
FIG. 3 is an enlarged partial cross-sectional view of the area surrounding the distal balloon waist of the balloon catheter of FIG. 1.

At the distal end of the shaft assembly 12 is a balloon assembly 14. The balloon assembly 14 includes an expandable balloon 28 having a proximal balloon waist length 30 and a distal balloon waist length 32. The proximal balloon waist 30 affixes the expandable balloon 28 to the outer tubular member 26 near its distal end by means of an adhesive, or alternatively, in combination with, RF, laser or other thermal bonding. The distal balloon waist 32, as shown in FIG. 2 and FIG. 3, similarly affixes the expandable balloon 28 to the inner tubular member 22 near its distal end by means of an adhesive or thermal bond (i.e., RF, laser or other thermal bonding). This particular balloon assembly 14 arrangement allows the expandable balloon 28 to be in fluid communication with the annular inflation lumen defined between the outer tubular member 26 and the inner tubular member 22. A portion of the inner tubular member 22 may extend distally beyond the distal balloon waist 32.

As described in detail above, the inner tubular member 22 and outer tubular member 26 can be formed of a polyamide material such as, for example, PEBAX®. The expandable balloon 28, on the other hand, can be formed of a polyester or aromatic polyester material such as polyethylene terephthalate. These two materials are sufficiently dissimilar in chemical composition to affect the bonding between them. In particular, the dissimilarities between the two material compositions may affect certain thermal bonding procedures. As a result, the effectiveness of the bond between the two structural components having been formed from these certain thermal bonding procedures may be structurally compromised.

Under certain circumstances, bonding failure may result in the separation of a portion of the distal balloon waist 32 from the inner tubular member 22 or separation of a portion of the proximal balloon waist 30 from the outer tubular member 26. During a procedure, such separation may result in an inflation fluid leak when such fluid is supplied. The balloon dilation catheter 10 is deployed once the catheter is properly advanced and positioned across a targeted site within a patient's anatomy. When in position, inflation fluid is directed through the catheter's annular inflation lumen into the expandable balloon 28. As the pressure within the expandable balloon 28 increases, fluid trapped within the expandable balloon 28 causes the expandable balloon's inflation. A fissure in the bond sealing the distal balloon waist 32 to the inner tubular member 22 or proximal balloon waist 30 to the outer tubular member 26 would result in a leak, thereby decreasing the inflation efficiency of the expandable balloon 28.

As with the distal balloon waist 32 bond, bonding may be more difficult between the proximal balloon waist 30 and the portion of shaft to which it is affixed depending upon the selection of each polymeric material. The present invention is discussed in detail with respect to the distal waist bond, but is understood to be equally applicable to the proximal waist 30 bond when dissimilar polymers are selected for the balloon and the portion of the shaft to which the proximal waist 30 is affixed.

With current manufacturing processes, the bonds formed between the distal balloon waist 32 and the inner tubular member 22 or proximal waist 30 and outer tubular member 26 are sufficiently strong to ensure a patient's safety during a medical procedure. The bonding between these two structural components, however, is a subject of constant improvement. Achieving the strongest bond possible when two dissimilar materials form their respective structural components assures the success of the medical device and the safety of the patient. As such, an improved bond is desired to further curb the concerns of both practitioners and patients alike regarding the functionality and safety of catheters using this design.

Success in bonding the distal balloon waist 32 to the inner tubular member 22 or the proximal waist 30 to the outer tubular member 26 has been traditionally achieved using an adhesive. In these traditional methods, the adhesive is first applied between the two components. The two components are then bonded together to form the completed sealed union. There exist drawbacks, however, to using adhesives in such bonding procedures. For example, adhesives that are suitable for joining the two catheter components are commonly associated with long curing times, sensitivity to ambient conditions (including humidity and temperature), and the need for extensive surface treatment. As a result, bonding between the distal balloon waist 32 and the inner tubular member 22 and the proximal balloon waist 30 and outer tubular member 26 is typically time and labor intensive.

Adhesives common in catheter manufacturing also often take hours to cure. Moreover, procedures for bonding the balloon waist to the tubular member are highly dependent on operator skill. Assemblers must initially apply the appropriate amount of adhesive between the two catheter components to insure proper adhesion. In certain embodiments, the assembler may then sculpt a backfill onto the bond using additional adhesive to provide a smooth transition. Assembler errors and curing times may result in substantial delays. Delays in catheter production increase the manufacturer's costs.

The present invention identifies the use of a selected group of polymeric materials that aid in bonding the distal balloon waist 32 to the inner tubular member 22 or the proximal balloon waist 30 to the outer tubular member 26. In effect, the selected group of polymeric materials "ties" the two structural components having differing material compositions together. Therefore, hereinafter, the layer of polymeric material disposed between either the distal balloon waist 32 and the inner tubular member 22 or the proximal waist 30 and the outer tubular member 26 is called a tie layer.

Tie layers suitable for the present invention possess a bonding affinity to both materials forming the proximal balloon waist 30, distal balloon waist 32, the inner tubular member 22, and the outer tubular member 26. Tie layer materials particularly suitable for the present invention include polyester and polyamide polymers. The tie layer may include a polyester and polyamide copolymer.

The polyester may be an aromatic polyester such as, for example, polyethylene terephthalate, polybutylene terephthalate, and the like. The polyester may be polyester elastomer such as, for example, copolymers having hard segments of polybutylene terephthalate or polyethylene terephthalate and soft segments including polytetramethylene oxide, poly 1,2-propylene or polyethylene oxide, and the like.

The polyamide may include polyamide elastomers including polyamide hard segments and polyether soft segments. The polyamide segments can include, for example, polyamide 11 and polyamide 12.

Although the difficulty in bonding the distal balloon waist 32 to the inner tubular member 22 and the proximal balloon waist 30 to the outer tubular member has been highlighted, other bonding areas along the catheter may be aided through tie layers. For example, a segment of tie layer may be placed between other portions experiencing bonding difficulties between a polyamide material and an aromatic polyester material.

Unlike traditional bonding procedures as discussed in detail above, a tie layer permits manufacturers to form a secured bond between the distal balloon waist 32 and the inner tubular member 22 and/or between the proximal balloon waist 30 and the outer tubular member 26 using thermal bonding processing alone. Adhesives, although they may still be used, are not required to form a secure bond. Thus, the inclusion of a tie layer when attaching the balloon assembly to the catheter shaft may decrease consumer costs by reducing the errors and curing times associated with traditional bond processing procedures.

FIG. 2 is an enlarged partial cross-sectional view of the area surrounding the distal balloon waist 32 of the balloon catheter 10 of FIG. 1 having a tie layer disposed therein. More specifically, two polymeric layers, a first layer 34 and a second layer 36, are shown disposed between the distal balloon waist 32 and the inner tubular member 22. Although two layers are specifically illustrated, a single tie layer is sufficient to form a sealably secure bond between the distal balloon waist 32 and the inner tubular member 22. Likewise, more than two tie layers may be disposed between the distal balloon waist 32 and the inner tubular member 22 in order to achieve a particular bonding and style configuration. Choosing the appropriate layer configuration often depends upon the specific materials utilized for the various structural components, as well as the desired shape for the distal tip of the catheter. This construction provides a PEBAX® to PET bond strength of 1.2 to 2.5 lbs in a tensile test as compared to 0.7 lbs without the above tie layer construction.

In certain embodiments, both the first layer 34 and the second layer 36 may comprise tie layer materials. For example, the first tie layer 34, because of its positioning adjacent the balloon 14 material, may possess a greater bonding affinity to materials forming a distal balloon waist 32, whereas the second tie layer 36 may possess a greater bonding affinity to materials forming an inner tubular member 22 and may be adjacent the shaft 12 material. Although either the first 34 or the second 36 tie layer may possess a bonding affinity to both the distal balloon waist 32 and the inner tubular member 22, the layer distribution as described may provide the maximum bonding efficiency for the region as a whole.

The first tie layer 34 may include a polyester material. The polyester material may include aromatic polyesters such as polybutylene terephthalate or a block copolymer including polybutylene terephthalate and polyether glycol. A commercially available polyester material is Hytrel® 7246 from DuPont.

The second tie layer 36 may include a polyamide material. The polyamide material may additionally include an aromatic polyester such as polybutylene terephthalate. A commercially available tie layer material is Grilamid EA20HV1 from EMS Chemie, Sumter, S.C. The second tie layer 36 may include a polyester and polyamide copolymer. The polyester may be an aromatic polyester such as, for example, polyethylene terephthalate, polybutylene terephthalate, and the like.

FIG. 3 is an enlarged partial cross-sectional view of the area surrounding the distal balloon waist of the balloon catheter of FIG. 1 having a tie layer disposed therein. More specifically, a single polymeric tie layer 35 is shown disposed between the distal balloon waist 32 and the inner tubular member 22. The single polymeric tie layer 35 can include polyester and polyamide polymers. The tie layer 35 may include a polyester and polyamide copolymer. The polyester may be an aromatic polyester such as, for example, polyethylene terephthalate, polybutylene terephthalate, and the like. The polyamide may be as described earlier.

Manufacturing a catheter distal tip, in accordance with the present invention, begins by first inserting a mandrel (not shown) into the distal end of the inner tubular member 22. The insertion of the mandrel insures against deformation of the catheter tip during the subsequent thermal processing events. Once the mandrel is inserted, the tie layers, preferably preformed as an insert, are disposed between the inner tubular member 22 and the distal balloon waist 32. In one embodiment, each tie layer is disposed over the inner tubular member 22, or alternatively, upon a preceding tie layer. The properly positioned tie layer is then thermally processed individually. In preferred embodiments, the tie layer insert is substantially the same length as the distal waist of the balloon, although it can be slightly longer or shorter and still provide adequate bonding. The short segment tie layer discrete to the balloon waist area provides a distinct advantage over the use of a tie layer over a greater length of the shaft in that the tie layer affects stiffness of the area in which it is used.

As shown in FIG. 2, multiple individual tie layers are disposed between the inner tubular member 22 and the distal balloon waist 32. Once the individual tie layers are properly positioned, they are all then thermally processed together, forming an effective fluid tight seal in the distal tip region of the catheter 10.

As shown in FIG. 2, a single polymeric insert comprising a plurality of tie layers 36, 34 is disposed between the inner tubular member 22 and the distal balloon waist 32. The tie layers 36, 34 within this polymeric insert may be thermally bonded during their extrusion process. The polymeric insert may be formed by extruding the plurality of tie layers into a tubular form (not shown). Multiple polymeric inserts are then derived from the single tubular extrusion by cutting the tubular extrusion at appropriate increments. Further, the polymeric inserts may be sized to fit the shaft utilizing a necking process after extrusion.

The present invention should not be considered limited to the particular examples described above, but rather should be understood to cover all aspects of the invention as fairly set out in the attached claims. Various modifications, and equivalent processes, as well as numerous structures to which the present invention may be applicable, will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What we claim is:

1. A balloon catheter assembly comprising:
   a polyamide tubular member having a proximal portion and a distal portion with a lumen extending between the proximal portion and the distal portion;
   a polyethylene terephthalate balloon having a proximal waist length, a distal waist length and an expandable region therebetween disposed about the distal portion; and
   a tie layer disposed between the proximal waist length or distal waist length and the first tubular member and having a length similar to the proximal waist length or the distal waist length, wherein the tie layer comprises a first polymer component and a second polymer component, the first polymer component possessing a greater bonding affinity for the polyethylene terephthalate balloon than does the second polymer component, the second polymer component possessing a greater bonding affinity for the first polyamide tubular member than does the first component.

2. The balloon catheter assembly according to claim 1, wherein the first component comprises a polyester.

3. The balloon catheter assembly according to claim 1, wherein the second component comprises a polyamide.

4. The balloon catheter assembly according to claim 1, wherein the first and second polymer components comprise a copolymer of polyester and polyamide.

5. The balloon catheter assembly according to claim 2, wherein the polyester comprises an aromatic polyester.

6. The balloon catheter assembly according to claim 2, wherein the polyester comprises a polyethylene terephthalate or a polybutylene terephthalate.

7. The balloon catheter assembly according to claim 2, wherein the polyester comprises a polyester elastomer.

8. The balloon catheter assembly according to claim 3, wherein the polyamide comprises a polyamide elastomer.

9. A method for improved bonding between an expandable balloon and a catheter shaft, the method comprising the steps of:
providing a first tubular member having a proximal portion and a distal portion with a lumen extending between the proximal portion and the distal portion;
providing a balloon having a proximal waist length, a distal waist length and an expandable region therebetween;
disposing a tie layer having a length similar to the proximal waist length or the distal waist length on the distal portion of the first tubular member, wherein the tie layer comprises a first component and a second component, the first component possessing a greater bonding affinity for the balloon than does the second component, the second component possessing a greater bonding affinity for the first tubular member than does the first component; and
disposing the balloon about the tubular member such that the tie layer is disposed between the proximal waist length or distal waist length and the first tubular member.

* * * * *